United States Patent [19]

Russell

[11] Patent Number: 4,521,513

[45] Date of Patent: Jun. 4, 1985

[54] PROTECTION AGAINST DENTAL CARIES

[75] Inventor: Roy R. B. Russell, Bromley, Northern Ireland

[73] Assignee: The Secretary of State of Social Services in Her Britannic Majesty's Government of the United Kingdon of Great Brtian and Northern Ireland, London, England

[21] Appl. No.: 466,336

[22] PCT Filed: Jun. 4, 1982

[86] PCT No.: PCT/6B82/00168

§ 371 Date: Feb. 3, 1983

§ 102(e) Date: Feb. 3, 1983

[87] PCT Pub. No.: WO82/04396

PCT Pub. Date: Dec. 23, 1982

[30] Foreign Application Priority Data

Jun. 19, 1981 [GB] United Kingdom ............... 8118886

[51] Int. Cl.³ .................... C12P 21/00; A61K 39/40; A61K 39/09; X12R 1/46
[52] U.S. Cl. ...................................... 435/68; 435/885; 424/85; 424/87; 424/88; 424/92; 260/112 R
[58] Field of Search ............... 424/177, 88, 87, 85, 424/86, 92, 50; 435/272, 259, 68, 253, 885; 260/112 R

[56] References Cited

U.S. PATENT DOCUMENTS 4,150,116  4/1979  Taubman et al. .............. 424/88
4,250,262  2/1981  Taubmanm et al. ........... 435/193

FOREIGN PATENT DOCUMENTS 2033223  5/1980  United Kingdom .
2060647  5/1981  United Kingdom ........... 424/92

OTHER PUBLICATIONS

Nesbitt, Warren et al. *Infection and Immunity* Apr. 1980 pp. 118-126 "*Association of Protein . . . S Mutans*".

Primary Examiner—Thomas G. Wiseman
Assistant Examiner—Robin Lynteskin
Attorney, Agent, or Firm—Cushman, Darby & Cushman

[57] ABSTRACT

An antigenic protein, termed antigen C, present on the cell walls and in cultures of *Streptococeus mutans*, especially genetic group I (serotypes c, e and f) is separated from other antigenic proteins, notably those which react heart tissue, to give an antigen preparation which may be used as a vaccine or to raise antibodies for use in protecting against dental caries. Antigen C is destroyed or extracted from the cell walls by treatment with boiling aqueous sodium dodecyl sulphate (10 gm per liter) for 10 minutes. It has a molecular weight of 70,000±5,000 and an isoelectric point of 4.45±0.24. It is destroyed by proteolytic enzyme and does not cross react with heart tissue. The antigen also occurs in the culture filtrate and/or cell extract and may readily be separated from these sources by affinity chromatography on immobilised antibody.

3 Claims, 3 Drawing Figures

PROTECTION AGAINST DENTAL CARIES

This invention relates to antigenic proteins derivable from the bacterial species *Streptococcus mutans*, and to preparations including such proteins for use in vaccines to reduce the incidence of dental caries.

*Streptococcus mutans* is believed to play an important role in the disease of dental caries and a number of laboratories have demonstrated that it is possible to reduce the level of caries in experimental animals by active immunisation with vaccine based on this bacterium. For example, it has been shown that in *Macaca fascicularis* monkeys fed a sucrose-rich diet a dramatic reduction in caries can be obtained following immunisation with either intact *S.mutans* or cell wall-rich material (Bowen, British Dental Journal, Vol 126, 1969, pp 159-160; Bowen et al. British Dental Journal, Vol 139, 1975, pp 45-50; Cohen et al. British dental Journal, Vol 147, 1979, pp 9-14). It has also been shown that no protection is obtained by using *S.mutans* cell walls which have been treated with trypsin to destroy proteins, thus indicating that it is probably a protein component of the *S.mutans* cell wall which is required for protective immunisation (Colman and Cohen, Pathogenic Streptococci, 1979, p 214, edited by M. T. Parker, Reedbooks, Chertsey, England).

In any immunisation procedure it is important to be able to recognise the bacterial component involved in protection. One obvious reason for this is that preparations can then be tested before use to ensure that the necessary component for protection is present. In addition, purification of the protective antigen permits preparation of a vaccine from which unwanted or toxic constituents can be excluded. Concern has been raised in the case of *S.mutans* by the demonstration that this organism possesses components which antigenically cross-react with mammalian heart tissue (see for example, Hughes et al., Infect Immun, 27, 1980, pp 576-588). Awareness of the existence of such heart cross-reactive antigens in *S.mutans* makes it desirable that they should be identified and chracterised, so that they can be excluded from vaccine preparations.

UK patent application No. 2033223A describes two proteins which are isolatable from cell walls of *S.mutans* and which exhibit antigenic behaviour. One of these antigenic proteins (labelled antigen A) is claimed in that application, the other (antigen B) having demonstrable cross-reactivity with heart tissue is believed to be unacceptable as a component of a vaccine for human use. Antigens A and B can be defined by the following set of criteria:

a. they are present on the cell walls of strains of *S.mutans* genetic group I (Coykendall, J Gen Microbiol 83, 1974, p 327). This genetic group contains strains of serotypes c, e and f as defined by Perch et al (Acta Path Microbiol Scand, B 82, 1974, p 357).

b. they remain present on said walls after boiling with 10 g/l sodium dodecyl sulphate (SDS) for 20 minutes.

c. as determined by SDS-polyacrylamide gel electrophoresis (SDS-PAGE) their apparent molecular weights are A: about 29,000; B, about 190,000.

d. as determined by isoelectric focussing in acrylamide gel, their isoelectric points are A: about 4.3; B: about 5.4, and, in the case of antigen A, the antigenic proteins e. are destroyed by proteolytic enzyme, and f. do not cross react wiht heart tissue.

We have now discovered that a further group of antigenic proteins (antigen C) can be isolated from cell walls of strains of *S.mutans* genetic group I. This group of proteins can be used to prepare monospecific antisera and appears to be involved in the protection against dental caries afforded by vaccination with cell walls of *S.mutans*. It has not shown any cross-reactivity with mammalian heart tissue.

Accordingly the present invention provides an antigen preparation for use in the reduction or prevention of dental caries comprising antigen C (as hereinafter defined), said preparation being substantially free from any heart cross-reactive antigens derivable from *S.mutans*.

Antigen C encompasses that group of antigenic proteins which:

a. are present on the cell walls of strains of *Streptococcus mutans* genetic group I (Coykendall) (i.e. serotypes c, e and f);

b. are destroyed or extracted by treatment of said cell walls with boiling aqueous sodium dodecyl sulphate (SDS) solution (10 gm/liter) for 10 minutes but remain associated with cell walls washed in SDS at 15° C.;

c. have a molecular weight of 70,000±5000 by SDS polyacrylamide gel electrophoresis (SDS-PAGE);

d. are destroyed by proteolytic enzyme;

e. have an isoelectric point of 4.45±0.24; and f. do not cross-react with heart tissue.

The present antigen preparation may contain antigen C as the only antigenic protein. In an alternative embodiment however, the preparation may contain antigen C in admixture with other non heart cross-reactive antigenic proteins, especially the antigen A described in our earlier UK patent application No. 2033233A.

The present antigen preparation may be used in the form of a pharmaceutical preparation, such as a vaccine, by the addition of suitable pharmaceutically acceptable diluents or carriers, such as adjuvants (e.g. aluminium hydroxide), stabilising agents and bacteriostats. Administration of a vaccine may be by subcutaneous, intramuscular, intraveneous or submucosal injection, typically at doses of 1-50 μg especially about 10 μg total antigens per Kg body weight. Immunisation may also be effected by an oral route e.g. by swallowing a capsule containing the antigen preparation or by repeated use of a mouthwash or toothpaste formulation containing antigen C.

It will be appreciated that the protection from dental caries afforded by the antigenic protein of this invention arises from the antibodies to this antigen produced by the body's immune response. Such antibodies can also be raised outside the subject to be immunised by conventional techniques such as injection of a suitable *S.mutans* antigen preparation including antigen C into e.g. cows or rabbits followed by exsanguination. Administration of antibody preparations produced in this way and including conventional pharmaceutically acceptable diluents or carriers is also effective in preventing or reducing dental caries. The present invention therefore includes antibody preparations which are specific for the antigenic determinants of antigen C or which contain antibodies to this antigen. It also includes pharmaceutical compositions comprising the antigenic preparations described above with conventional diluents or carriers and also compositions comprising the antibodies to antigen C with such diluents or carriers.

Antigen C is present both on the cell wall and in the cell free culture filtrates of S.mutans. It can be extracted from the cell walls of S.mutans by an adaptation of conventional techniques used for removing proteins from cell structures but it is preferably separated from either cell-free culture filtrates or whole cell extracts of S.mutans which in general contain fewer substances that are likely to interfere with purification procedures.

According to another aspect of the present invention, therefore, there is provided a process for producing an antigen preparation for use in the reduction or prevention of dental caries comprising antigen C, said preparation being substantially free from any heart cross reactive antigens derivable from Streptococcus mutans comprising growing bacteria of Streptococcus mutans in a suitable culture medium, removing at least the cell walls from the resulting culture to leave a protein solution and separating the required antigen preparation from said protein solution.

Separation by column chromatography using appropriate gel permeation, ion exchange or hydrophobic interaction materials is possible but it is preferred to use a separation process which includes the step of affinity chromatography on immobilised antibody to antigen C. The immobilised antibody may be either monospecific antibodies to antigen C or one or more monoclonal antibodies to antigen C prepared by cell hybridisation techniques.

If a mixture of antigen C and antigen A is required then the two antigens may be separately prepared by affinity chromatography on immobilised antibody and then combined, or the mixture may be prepared in one step by affinity chromatography on a combination of anti-antigen C and anti-antigen A immobilised antibody.

The culture medium may be any conventional medium for S.mutans, such as Todd-Hewitt broth, tryptone/yeast extract or a chemically defined medium. For ease of subsequent purification a chemically defined medium is preferred. Antigen C is released into the growth medium at all stages of the culture. The cells may be grown in batch culture and, preferably, harvested at early stationary phase (typically 15-25 hr at 37° C.). Alternatively the cells may be grown in continuous culture, preferably at a dilution rate of between about 0.01 and 0.1, especially about 0.05, $hr^{-1}$.

The protein solution may comprise culture filtrates, obtained by removing whole cells, or a cell extract, freed from cell walls and debris. Alternatively, it may be a mixture of these produced by disrupting the cells of a whole culture and subsequently removing cell walls and debris. The cell walls may be removed, either as whole cells or as fragments following disintegration, by conventional techniques, such as centrifugation or filtration.

DESCRIPTION OF THE DRAWINGS

Typical products and processes in accordance with the present invention will now be described by way of example only with reference to the accompanying drawings in which.

Antigen C

1. Production of cell walls

Figure 1:
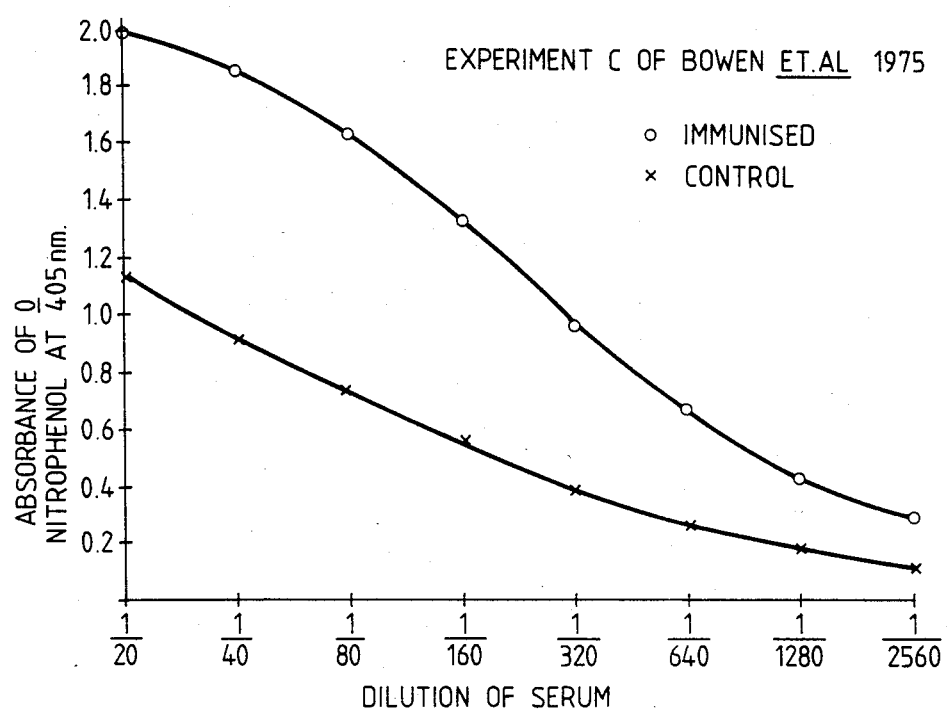
FIG. 1 illustrates the titration by ELISA of serum IgG antibody to antigen C in four control monkeys and four monkeys immunised with cell walls, (as described by Bowen et al, 1975 (experiment C)), by plotting the absorbance of p-nitrophenol at 405 nm against serum dilution, FIG. 2 compares the development of caries in the permanent dentition of three monkeys (Macaca fascicularis) immunised with cell walls of S.mutans with that in five control animals (as described in Cohen et al, 1979, (experiment 19), and FIG. 3 illustrates the titration by ELISA of serum IgG antibody to antigen C in four control monkeys and four monkeys immunised with cell walls (as described in Cohen et al, 1979 (experiment 19), by plotting the absorbance of p-nitrophenol at 405 nm against serum dilution.

S.mutans of the widely known strain Ingbritt was used. This strain has been described by Krasse (Archs Oral Biol, 11, 1966, pp 429-436) and is classified as genetic group I by Coykendall and serotype c according to Perch et al. This strain has been deposited with the National Collection of Industrial Bacteria, Aberdeen, Scotland, as NCIB 11516. Similar results have been obtained using a strain from the National Collection of Type Cultures, Colindale, London (NCTC 10449) which is closely related to strain Ingbritt.

The bacteria were grown in the medium described by Ellwood et al, (Archs Oral Biol 19, 1974, pp 659-664) in a 600 ml chemostat at a dilution rate of 0.05 $hr^{-1}$, the pH being maintained at 6.5 by automatic addition of potassium hydroxide. Bacteria were collected by centrifugation, washed in saline and heated at 60° for 30 min to inactivate autolytic enzymes. They were then broken by shaking with No 12 Ballotini glass beads in a Mickle Tissue Disintegrator. The broken cells were separated from glass beads by filtration and washed twice with water and twice with 1M NaCl before being resuspended in SDS (10 g/l) in water by means of a Potter tissue homogeniser. Intact bacteria were separated from walls by low-speed centrifugation and the walls washed extensively in saline and water before being freeze-dried.

Similar results have been obtained using bacteria grown batch-wise in Todd-Hewitt broth (J Path. and Bacteriol, 35, 1932, pp 973-974) or a medium containing glucose, tryptone and yeast extract with controlled pH and either breaking the cells in a Braun homogeniser or else subjecting them to a more prolonged extraction with SDS at room temperature.

2. Preparation of Antiserum

Freeze-dried walls were suspended in sterile saline at a concentration of 1 mg/ml and used to immunise monkeys (see below) or rabbits. Rabbits received 3 intramuscular injections, 3 weeks apart, each of 1 mg walls in saline containing 10% aluminium hydroxide adjuvant. They were then exsanguinated by cardiac puncture 1 week after the final injection.

3. Immunoelectrophoresis experiments

Antiserum to cell walls prepared as described above were used both in the characterisation and purification of antigen C. When the proteins from a culture filtrate of strain Ingbritt (or related strains) was used as antigen in a crossed immunoelectrophoresis experiment performed according to methods described by Axelsen et al, (in "A Manual of Quantative Immunoelectrophoresis, OSLO, 1973) and electrophoressed into antiserum to walls, three precipitation peaks were observed. By means of experiments using intermediate gel techniques (Axelsen et al, p 71) with the intermediate gel containing either antigen A and B or monospecific antisera to A and B, it was possible to show that two of the precipitation peaks were due to antigens A and B, the third to an urelated antigen, namely C.

In order to investigate the nature of antigen C, the antigen preparation was subjected to various treatments before being examined by crossed immunoelectrophoresis. It was found that antigen C was destroyed by incubation for 3 hrs at 37° C. with 200 μg/ml of the proteolytic enzymes trypsin or pronase. Antigen C is thus protein in nature. Samples of antigen C were also destroyed by exposure to buffers of pH less than 5.0 for 3 hrs with suggestions that it is also acid-labile.

Information on the physical properties of antigen C was obtained by crossed immunoelectrophoresis in which the first dimension separation was by SDS-polyacrylamide gel electrophoresis to separate proteins according to molecular weights (details of method in Russell, J Gen Microbiol 114, 1979, 109–115) or by crossed immunoelectrofocussing in agarose (Rosen and Aman, J Immunol Meth, 1979, 28, 1) where proteins are separated according to their charge. The results indicated that antigen C had an apparent molecular weight of 70,000± 5000 (SD) and an isoelectric point of 4.45±0.24.

Antigen C could also be detected by immunodiffusion experiments with antiserum to walls or pure antigen C (see below). Immunodiffusion was therefore used to demonstrate that antigens identical to C were produced by 6 other strains of *S.mutans* serotype c and also by representatives of serotypes e and f.

4. Purification of Antigen C

The data presented above show that antigen C is present both on the cell wall and in a cell-free culture filtrate. Although antigen C can be extracted from walls by appropriate means it is preferable to purify it from culture filtrate as this will contain fewer substances likely to interfere with purification procedures.

Whilst antigen C may be purified by the routine laboratory procedures of column chromatography using, for example, appropriate gel permeation and ion exchange matrices, it can most conveniently be isolated by immunosorbent affinity chromatography, and protocols based on this technique are presented below.

a. *S.mutans* strain Ingbritt was grown in a semi-defined medium (Russell, FEMS Microbiol Lett 6, 1979 pp 197–199) to early stationary phase and cells removed by centrifugation followed by filtration through glass fibre. The protease inhibitor phenyl methyl sulphonyl fluoride (PMSF) was added at a final concentration of 1mM, along with sodium azide (final 0.02%) to inhibit bacterial growth. The filtrate was then passed through an affinity chromatography column containing the insoluble glucose polymer mutan and agarose gel beads (Sepharose CL-6B) prepared essentially as described by Russell (J Gen, Microbiol, 112, 1979, pp 197-201) in order to remove the glucosyltransferase enzymes and other dextran-binding proteins which may otherwise bind to subsequent immunosorbent columns (Russell, FEMS Microbiol, Lett, 1981, 11, 279). The culture filtrate was then passed in sequence through a series of three immunosorbent columns containing
 (i) monospecific antibody to antigen A,
 (ii) monospecific antibody to antigen B,
 (iii) cell walls.

The third column thus contained antibody to antigens A, B and c but as antigens A and B are removed from the sample before reaching the third column only antigen C was retained and could subsequently be eluted with an appropriate agent such as 3M sodium thiocyanate. Immunosorbent columns were prepared by standard methods in which immunoglobulin G fractions of sera were coupled to cross-linked agarose beads (CnBr-activated Sepharose 4B, Pharmacia Fine Chemicals Ltd) by the manufacturers' recommended procedures.

Antigen C prepared by the above means was then used to raise monospecific antiserum, allowing the construction of C-specific immunosorbent columns which permitted purification of the antigen in a single step.

b. An alternative procedure for the purification of antigen C involved immunosorbent affinity chromatography followed by hydrophobic interaction chromatography. In this method a culture filtrate was passed first through an affinity column containing mutan and sepharose, then through an immunosorbent column containing antibody to cell walls. Antigens A, B and C were retained by such a column and could be eluted with 3M sodium thiocyanate in 0.05M Tris HCl buffer (pH 7.5). The sodium thiocyanate was removed by dialysis and the solution of antigenic proteins equilibrated in 0.05M Tris HCl buffer (pH 7.5) containing 1M ammonium sulphate. This sample was then applied to a chromatography column containing Phenyl Sepharose CL-4B (Pharmacia Fine Chemicals). Proteins retained by the column were then eluted by a gradient of decreasing ammonium sulphate concentration and concurrently increasing ethylene glycol concentration (final concentration 0% and 50% respectively). Antigen C was eluted between 0.6 and 0.7M ammonium sulphate/15–20% ethylene glycol, in advance of antigens A and B.

Antigen C prepared by the above means was then used to raise monospecific antiserum, allowing the construction of C-specific immunosorbant columns which permitted purification of the antigen in a single step.

Protection against caries by immunisation with cell walls

Immunisation with cell walls of *S.mutans* strain Ingbritt prepared as described above has been found in two separate experiments to confer protection against caries in monkeys (*Macaca fascicularis*) and details of these experiments have been published by Bowen et al. (British Dental Journal 1975, Vol 139, pp 45–58) and Cohen et al. (British Dental Journal, 1979, Vol 147, pp 9–14).

In experiment C as described by Bowen et al 5 control animals maintained on a caries-promoting diet were compared with 4 animals immunised with cell walls. Five years after the start of the experiment the total number of carious lesions in the control animals was 64, while in the immunised group a total of only 4 lesions was detected. This protection was maintained for at least 9 years (Cohen et al, 1979). Examination of samples of serum from experimental animals taken 5 years after the start of the experiment by crossed immunoelectrophoresis showed that immunisation with cell walls had induced antibody to antigens A, B and C. This sensitive technique failed to reveal the existence of antibody to any further antigens.

Quantitation of antibody responses was performed by enzyme-linked immunosorbent assay (ELISA), following the microplate technique of Voller et al (1977, Flowline Publications). Plastic microtitre trays were coated with pure antigen C at a concentration of approximately 1 μg/ml.

Assay of the amount of monkey antibody binding to antigen was achieved by incubating with anti-human IgG conjugated to alkaline phosphatase (Sigma Chemical Co) and measuring the consequent production of a chromophore (p-nitrophenol) by measuring its absorbance at 405 nm. FIG. 1 shows the results of titration of antisera from control and immunised groups of monkeys. The results are given in tabular form in Table 1. Immunisation with cell walls resulted in a significant increase in level of antibody to antigen C. It may be noted that it has previously been shown that even non-immunised control animals develop antibody to S.mutans antigens with age (Russell and Beighton, Infection & Immunity 1981, Vol 35, pp 741-744).

TABLE 1

| Dilution | Control | Immunised |
|---|---|---|
| 1/20 | 1.35 ± 0.275 | 1.996 ± 0.01 |
| 1/40 | 0.91 ± 0.21 | 1.859 ± 0.09 |
| 1/80 | 0.747 ± 0.21 | 1.64 ± 0.21 |
| 1/160 | 0.566 ± 0.13 | 1.33 ± 0.29 |
| 1/320 | 0.386 ± 0.09 | 0.968 ± 0.27 |
| 1/640 | 0.262 ± 0.06 | 0.677 ± 0.20 |
| 1/1280 | 0.18 ± 0.05 | 0.430 ± 0.13 |
| 1/2560 | 0.115 ± 0.03 | 0.296 ± 0.08 |

Figure 2:
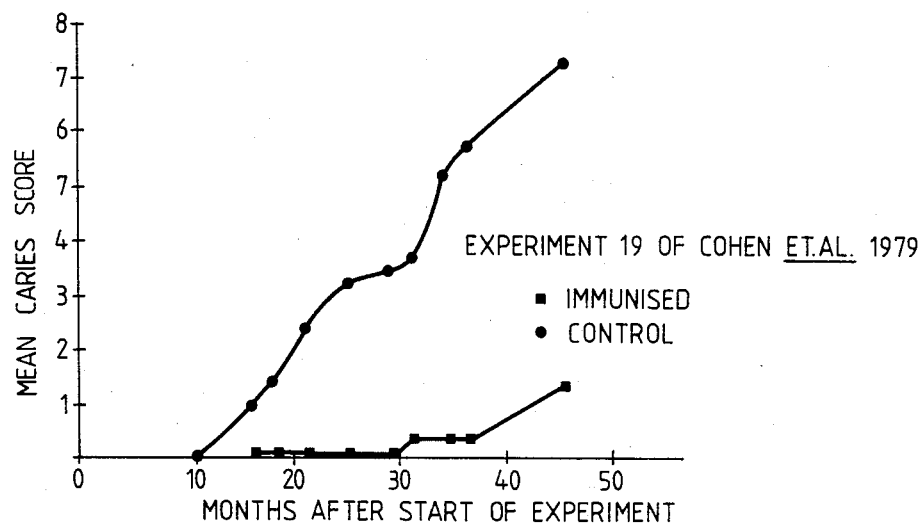

In experiment 19 described by Cohen et al (1979) a group of control monkeys were compared with groups immunised with cell walls prepared from S.mutans strain Ingbritt grown in a chemostat at a dilution rate (D) of 0.05 hr$^{-1}$. The progression of caries in these animals is illustrated in FIG. 2 and shows that walls from cells grown at D=0.05 hr$^{-1}$ conferred significant protection. The results are given in tabular form in Table 2.

TABLE 2

| Time from start of experiment (months) | Mean caries score ± SE | |
|---|---|---|
| | Control | Immunised |
| 11 | 0 | 0 |
| 16 | 1.0 ± 0.45 | 0 |
| 18 | 1.4 ± 0.75 | 0 |
| 21 | 2.4 ± 0.97 | 0 |
| 25 | 3.2 ± 1.88 | 0 |
| 29 | 3.4 ± 1.63 | 0 |
| 31 | 3.6 ± 1.60 | 0.33 ± 0.3 |
| 34 | 5.2 ± 1.67 | 0.33 ± 0.3 |
| 36 | 5.75 ± 1.86 | 0.33 ± 0.3 |
| 45 | 7.25 ± 2.62 | 1.33 ± 0.29 |

Figure 3:
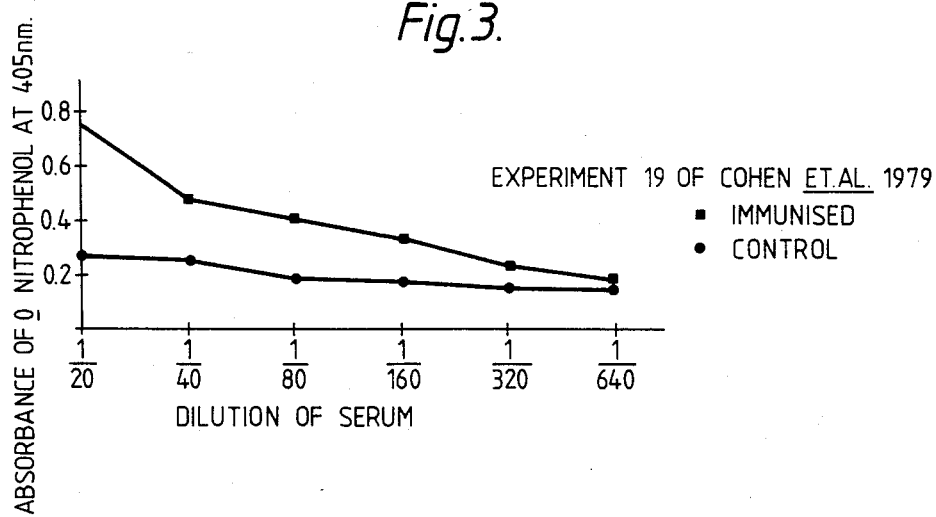

The levels of antibody to antigen C in serum samples taken at various stages of the experiment were measured by ELISA. Throughout the experiment it was found that animals immunised with walls from cells grown at D=0.05 h$^{-1}$ had elevated titres of antibody to antigen C and these titres were significantly higher than in the control animals. Representative results obtained with serum samples taken 3 years after the start of the experiment are shown in FIG. 3. The results are given in tabular form in Table 3.

There is a strong correlation between the induction of a high level of antibody to antigen C and protection against caries.

TABLE 3

| Dilution | Control | Immunised |
|---|---|---|
| 1/20 | 0.262 ± 0.08 | 0.752 ± 0.15 |
| 1/40 | 0.253 ± 0.07 | 0.478 ± 0.08 |
| 1/80 | 0.188 ± 0.04 | 0.400 ± 0.05 |
| 1/160 | 0.173 ± 0.04 | 0.330 ± 0.04 |
| 1/320 | 0.144 ± 0.02 | 0.228 ± 0.04 |
| 1/640 | 0.145 ± 0.03 | 0.181 ± 0.04 |

Antibody responses of immunised monkeys

Serum from animals immunised with cell walls contained antibodies to antigen C. Such antibodies could readily be demonstrated by immunodiffusion or immunoelectrophoresis experiments utilising pure antigen C. No such antibody could be observed in serum from control non-immunised animals. It is thus apparent that the existence of antibody to C correlates with protection in monkeys immunised with cell walls.

Experiments on immunisation of monkeys with various vaccine preparations have been in progress in these laboratories for over 12 years. Serum samples from many animals in these experiments are still available, and were examined for their presence of antibody to antigen C. The results are summarised below in Table 4 and confirm the correlation between presence of antibody to C with protection.

TABLE 4

| Experiment No | Vaccine | Reduction in caries | Antibody to C |
|---|---|---|---|
| 4 | walls | 100% | + |
| 11 | cells | 50% | + |
| 14 | cells | 60% | + |
| 17 | GTF (Glucosyl transferase) | 0 | − |
| 19 (30 months) | walls | 100% | + |

I claim:

1. A process for producing an antigen preparation, for use in the reduction or prevention of dental caries, from bacteria of the group Streptococcus mutans genetic group I, the preparation being substantially free from any heart cross reactive antigens derivable from Streptococcus mutans, wherein the process comprises growing bacteria of the group Streptococcus mutans genetic group I in a culture medium to produce a cell culture, removing at least the cell walls from the cell culture to leave a protein solution and separating the antigen preparation from the protein solution by a method of separation which comprises contacting the protein solution with immobilized antibody, washing unwanted materials from the immobilized antibody under such conditions that the antigen preparation is retained on the immobilized antibody and eluting the antigen preparation from the immobilized antibody under such conditions that the antibody remains in an immobilized state and the antigen preparation retains its antigenicity, wherein the immobilized antibody has a specificity for one or more antigenic proteins which have the following properties: they
 (a) are present on the cell walls of strains of Streptococcus mutans genetic group I;
 (b) are destroyed or extracted by treatment of said cell walls with boiling aqueous sodium dodecyl sulphate (SDS) solution (10 gm per liter) for 10 minutes but remain associated with said cell walls after treatment of the walls with aqueous SDS solution (10 gm per liter) at 15° C.;
 (c) have a molecular weight of 70,000±5,000 by SDS-polyacrylamide gel electrophoresis (SDS-PAGE);
 (d) are destroyed by proteolytic enzyme;
 (e) have an isoelectric point of 4.45±0.24; and
 (f) do not cross react with heart tissue.

2. A process according to claim 1 wherein the immobilized antibody comprises a combination of antibodies, the first having a specificity for one or more antigenic proteins which have the following properties: they
  (a) are present on the cell walls of strains of *Streptococcus mutans* genetic group I;
  (b) are destroyed or extracted by treatment of said cell walls with boiling aqueous sodium dodecyl sulphate (SDS) solution (10 gm per liter) for 10 minutes, but remain associated with said cell walls after treatment of the walls with aqueous SDS solution (10 gm per liter) at 15° C.;
  (c) have a molecular weight of 70,000±5,000 by SDS-polyacrylamide gel electrophoresis (SDS-PAGE);
  (d) are destroyed by proteolytic enzyme;
  (e) have an isoelectric point of 4.45±0.24; and
  (f) do not cross react with heart tissue;

the second having a specificity for one or more antigenic proteins which have the following properties: they
  (a) are present on the cell walls of strains of *Streptococcus mutans* genetic group I;
  (b) remain associated with said cell walls after boiling with aqueous SDS solution (10 gm per liter) for 20 minutes;
  (c) have a molecular weight of 29,000 by SDS-polyacrylamide gel electrophoresis (SDS-PAGE);
  (d) have an isoelectric point of about 4.3;
  (e) are destroyed by proteolytic enzyme; and
  (f) do not cross react with heart tissue.

3. A process according to claim 1 wherein the bacteria is a strain of *Streptococcus mutans* serotype C.

* * * * *